(12) United States Patent
Giuntoli et al.

(10) Patent No.: US 7,171,276 B2
(45) Date of Patent: Jan. 30, 2007

(54) HYDROGEL AND SCRIM ASSEMBLY FOR USE WITH ELECTRO-ACUPUNCTURE DEVICE WITH STIMULATION ELECTRODES

(75) Inventors: David M. Giuntoli, Carlsbad, CA (US); Thomas L. Grey, Carlsbad, CA (US); Gregory J. Gruzdowich, Carlsbad, CA (US); Benjamin W. Wang, Carlsbad, CA (US)

(73) Assignee: Abbott Laboratories, Abbott Park, IL (US)

( * ) Notice: Subject to any disclaimer, the term of this patent is extended or adjusted under 35 U.S.C. 154(b) by 788 days.

(21) Appl. No.: 09/896,977

(22) Filed: Jun. 29, 2001

(65) Prior Publication Data

US 2003/0069627 A1 Apr. 10, 2003

(51) Int. Cl.
*A61N 1/04* (2006.01)
(52) U.S. Cl. .................................... 607/153
(58) Field of Classification Search ........... 607/152–3, 607/148–9, 153, 149; 600/391–392
See application file for complete search history.

(56) References Cited

U.S. PATENT DOCUMENTS

| | | | | |
|---|---|---|---|---|
| 4,981,146 A | | 1/1991 | Bertolucci | 128/802 |
| 5,085,217 A | * | 2/1992 | Shimizu | 600/391 |
| 5,115,801 A | | 5/1992 | Cartmell et al. | 602/48 |
| 5,328,455 A | | 7/1994 | Llyod et al. | 604/20 |
| 5,511,548 A | | 4/1996 | Riazzi et al. | 128/641 |
| 5,921,925 A | | 7/1999 | Cartmell et al. | 600/391 |
| 5,938,597 A | | 8/1999 | Stratbucker | 600/382 |
| 6,076,002 A | * | 6/2000 | Cartmell et al. | 600/372 |

FOREIGN PATENT DOCUMENTS

| | | |
|---|---|---|
| EP | 0455324 | 7/1995 |
| EP | 0528091 | 2/1997 |
| EP | 0547833 | 11/1997 |
| EP | 0530982 | 2/1998 |

\* cited by examiner

*Primary Examiner*—Angela D. Sykes
(74) *Attorney, Agent, or Firm*—David L. Weinstein (57) ABSTRACT

A hydrogel and scrim assembly adapted for use with an electro-acupuncture device to enhance electrical conduction between the device and the skin and to provide an impedance matching layer between the device and the skin. The assembly includes a scrim with conductive hydrogel masses disposed on the surface of the scrim. The hydrogel masses are sized and dimensioned so that when the pad is adapted to the device, the hydrogel masses do not bridge the electrodes to cause a short between the electrodes.

7 Claims, 7 Drawing Sheets

HYDROGEL AND SCRIM ASSEMBLY FOR USE WITH ELECTRO-ACUPUNCTURE DEVICE WITH STIMULATION ELECTRODES

FIELD OF THE INVENTIONS

The devices described below relate to the field of electro-acupuncture and non-invasive stimulation of nerves, and more particularly to hydrogels for application adhesively between electrodes and a patient's skin to provide electrical contact therewith.

BACKGROUND OF THE INVENTIONS

We have developed an electro-acupuncture device which has proven effective for the control of nausea and vomiting. The device, marketed under the trademark Relief-Band®, is worn on the wrist like a wristwatch, with a watch-like housing which is positioned on the underside of the wrist. The device is described in Bertolucci, Nausea Control Device, U.S. Pat. No. 4,981,146 (Jan. 1, 1991), and in our co-pending application Electro-Acupuncture Device with Stimulation Electrode Assembly, filed Nov. 22, 2000, and incorporated herein in its entirety. The housing has two electrodes on the inside face (the face in contact with the wrist when secured to the wrist), a battery and circuitry inside the housing, and control buttons on the outer face. A patient suffering from nausea or vomiting (from motion sickness, morning sickness, chemotherapy, or anesthesia) can strap the device onto their wrist and turn it on. When turned on, the device emits an electrical stimulation pulse over the P6 acupuncture point (corresponding to the superficial course of the meridian nerve through the wrist). Within several minutes, most patients experience a substantial relief of nausea. The device uses non-invasive nerve stimulation whereby electricity is passed through two electrodes to stimulate nerves located on the ventral side of the wrist (this anatomical position is sometimes referred to as the palmar side of the wrist). The treatment provided by the device is sometimes referred to as electro-acupuncture, which is a form of acupuncture, and the ventral site of application is referred to in the acupuncture art as the P6 point, pericardium 6 point, or master point of the pericardium meridian (sometimes referred to as the vascular meridian). A primary object of the invention is to provide a non-chemical, non-invasive, painless and inexpensive method of alleviating nausea. The device is also portable, self-contained and convenient to the patient. Electrical pulse repetition rate of approximately 70 pulses per second and a pulse width of 80 microseconds has been found to provide effective relief of nausea in a patient. Our currently preferred electrical pulse pattern comprises about 350 microsecond pulse width at about 31 pulses per second at power levels of about 10–35 milli-amps peak pulse height. Thus a wide range of pulse patterns may be used in non-invasive nerve stimulation devices.

The stimulation and effect of our electro-acupuncture products are greatly enhanced if a conductive gel is used in conjunction with the electro-acupuncture device. This gel serves as an electronic to ionic current conversion layer (or an impedance matching layer) between the electrodes and the dry outer skin layer. This electrical conduction layer, sometimes referred to as an impedance matching layer, greatly enhances the effect of the device and lowers the power requirements for the device. The patient applies the gel to the skin before strapping the device onto the wrist. The gel may be referred to as a conductivity gel or an electromedical coupling agent.

Hydrogel is a common component used in medical electrode devices. Riazzi et al., Biomedical Electrode Having A Secured One-Piece Conductive Terminal, U.S. Pat. No. 5,511,548, discloses an assembly comprising a conductive hydrogel layer having two surfaces, one surface adapted to adhesively contact the skin, a porous scrim applied to the other surface of the hydrogel layer for support of the hydrogel layer, and an electrode integrally attached to the scrim and in contact with the hydrogel layer through the pores of the scrim. The assembly provides for electrical conduction from the one electrode, through the pores to the hydrogel layer, and to the skin. Stratbucker, Electrocardiograph Bioelectric Interface System and Method of Use, U.S. Pat. No. 5,938,597 discloses a pair of EKG electrodes covered by a single sheet of hydro-polymer. A slit is present in the hydro-polymer sheet and in between two electrodes. The slit prevents transmission of EKG signals at one electrode to the other electrode through the gel layer.

A limitation on the use of a conductive hydrogel with our electro-acupuncture device is that it is possible for some users to apply too little of the gel and thus reduce the effectiveness of the device. Additionally, applying too much hydrogel can cause the electrodes to short, thereby reducing the effectiveness of the device. The gel can also be washed away or rubbed off during use. Some users find the gel too messy and inconvenient to deal with. As a result, the user may abandon the device in favor of the drugs intended to be replaced by the device. As an alternative to the gel, we have developed a hydrogel coating which adheres to the electrodes and can be applied to the electrodes during manufacture or by the user. The provision of the hydrogel during manufacture enhances effectiveness of the device since it eliminates the possibility that some users will apply too much gel or too little gel. The provision of the hydrogel pad in user-replaceable form also enhances effectiveness eliminating the possibility that some users will apply too much gel or too little gel.

SUMMARY

We have developed a hydrogel pad or patch for use with an electro-acupuncture device having stimulation electrodes. When applied to the device, the hydrogel provides an electrical conduction layer (or an impedance matching layer) between the device and the user's skin. The hydrogel patch is comprised of conductive gel or hydrogel secured to the top and/or bottom surfaces of a sufficiently porous scrim. The hydrogel is semisolid and can be shaped and sized as layers, dots, spheres, or strips. The hydrogel permeates into the pores of the scrim such that the hydrogel is present on both surfaces. When the hydrogel pad is releasably applied to the device and the device is secured to the skin, the hydrogel contacts both the electrodes and the skin to provide an electrical conduction between the electrodes and the skin. Alternatively, the hydrogel patch is comprised of hydrogel applied to a scrim provided it the form of a hard non-porous carrier having precisely spaced holes punched through the carrier or precisely spaced electrode-shaped cutouts in the carrier. Hydrogel is secured over the holes or cutouts such that the hydrogel is present on both surfaces of the carrier. The hydrogel is shaped and spaced on the scrim or carrier such that the hydrogel does not bridge the electrodes to short the electrodes while maintaining suitable contact with the electrodes and skin.

BRIEF DESCRIPTION OF THE DRAWINGS

FIG. 5a is an exploded view of the hydrogel pad having a non-porous carrier with holes punched through.

DETAILED DESCRIPTION OF THE INVENTIONS

Figures 1, 2:
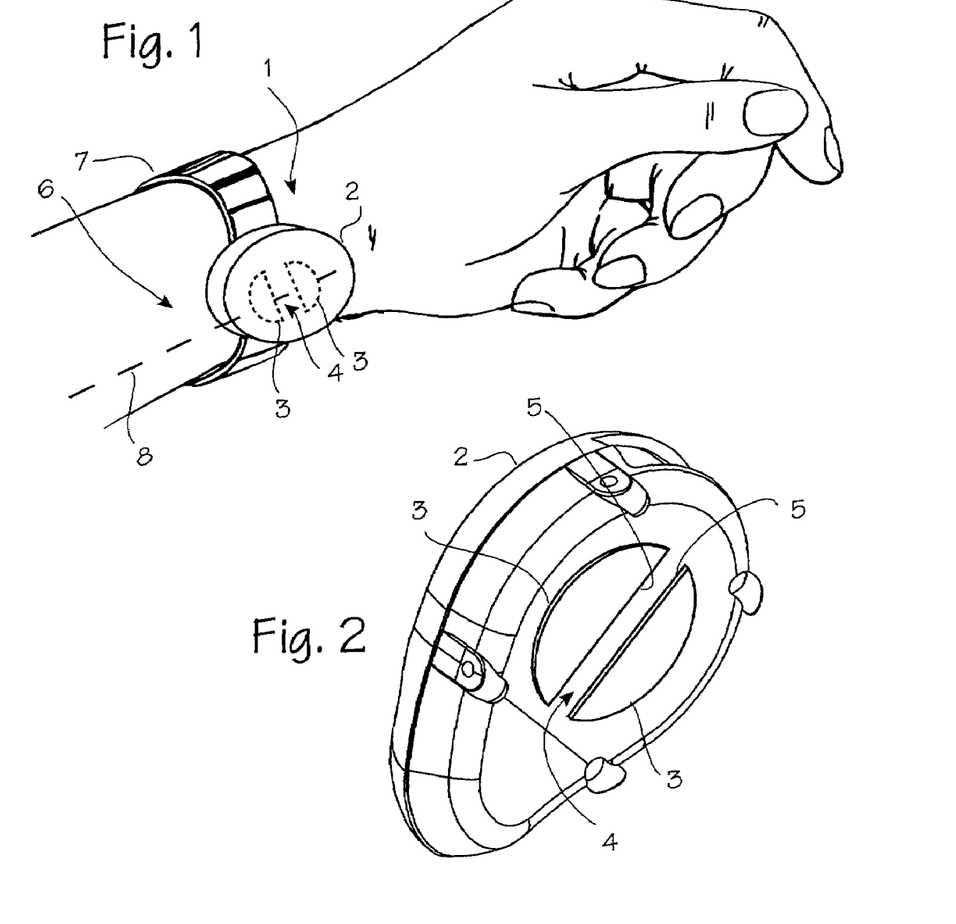
FIG. 1 is a view of the electro-acupuncture device in use on the wrist of a patient.
FIG. 2 is a view of the bottom of the electro-acupuncture device.

FIG. 1 illustrates an electro-acupuncture or non-invasive nerve stimulation device 1 in use on the wrist of a patient. The basic nerve stimulation device is described in Bertolucci, Nausea Control Device, U.S. Pat. No. 4,981,146 (Jan. 1, 1991), and is incorporated herein in its entirety. FIG. 2 is a view of the underside of the nerve stimulation device. The nerve stimulation device is comprised of a housing 2. The required battery and control electronics are housed within the housing, and input mechanisms (push buttons, dials, and the like) are located on the outer face of the housing. The stimulation device is further comprised of a pair of electrodes 3 attached to the bottom outer surface of the housing. The electrodes are separated apart from each other such that there is an inter-electrode gap 4 along opposing edges 5 of the electrodes. The inter-electrode gap separates the electrodes to prevent a short circuit between the electrodes. The nerve stimulation device is secured to the ventral side of the wrist 6 with a strap 7 such that the pair of electrodes is disposed over the median nerve 8 (indicated by the phantom line) and in contact with the skin in the vicinity of the P6 acupuncture point. The electrodes cover an area of about 1 inch (2.5 cm).

Figure 3:
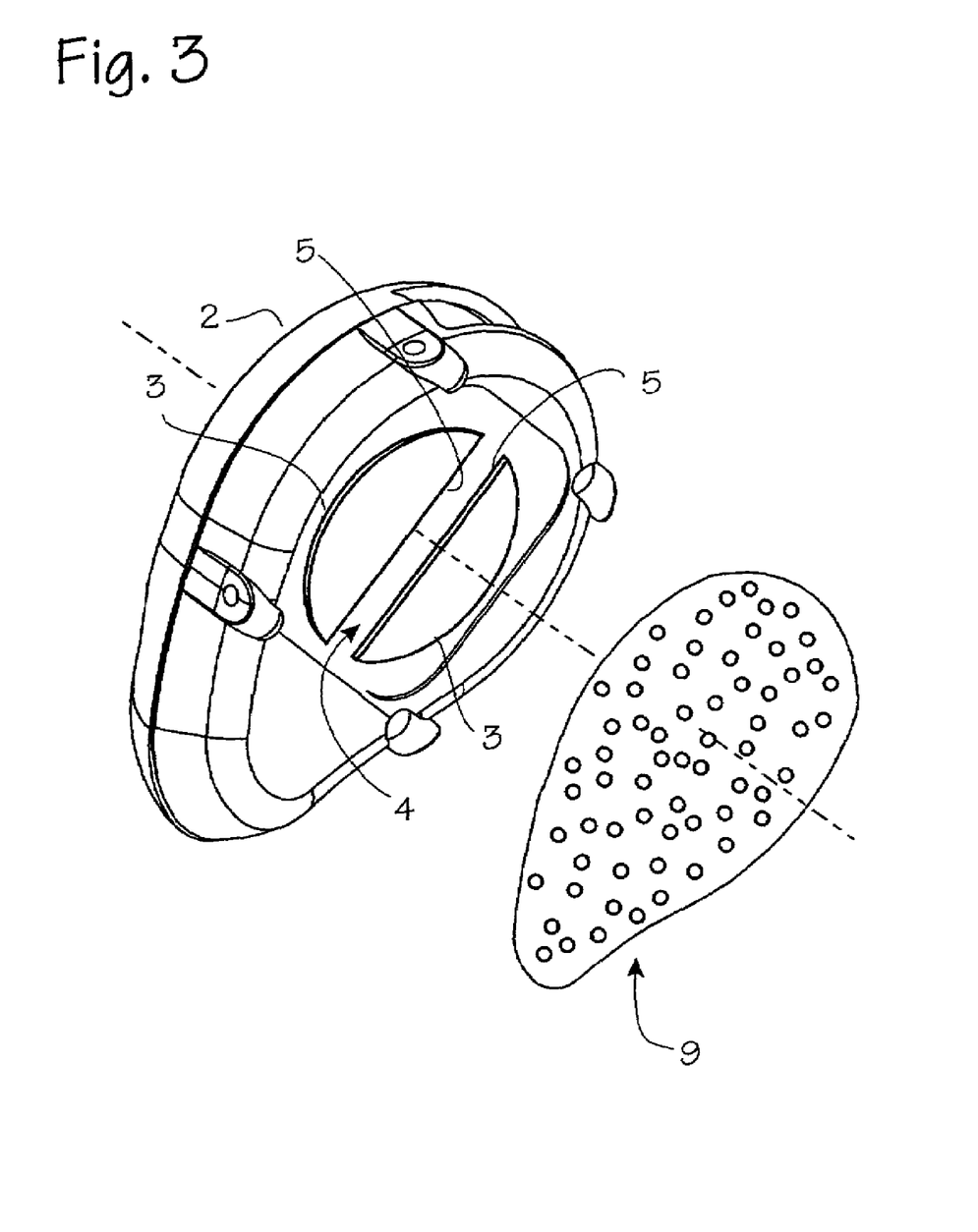
FIG. 3 is a bottom view of the electro-acupuncture device and the hydrogel pad.

FIG. 3 is a view of the nerve stimulation device 1 and a hydrogel pad or patch 9. The hydrogel pad can be releasably applied to the device at the bottom of the housing 2 and over the pair of electrodes 3. When the hydrogel pad is properly applied to the device and the device is secured to the wrist, the hydrogel pad contacts the pair of electrodes and provides a conductivity enhancing layer (sometimes referred to as an impedance matching layer) between the device and the user's skin. Since the hydrogel pad is releasably applied to the device, the hydrogel pad can be easily removed from the device when the device is not in use or when the hydrogel pad is worn out. When the hydrogel pad is not in use, one or two protective sheets of plastic can be applied over the surfaces of the hydrogel pad to protect the hydrogel dots from drying and fouling. When needed, the user can peel the protective sheets off the hydrogel pad.

Figure 4A:
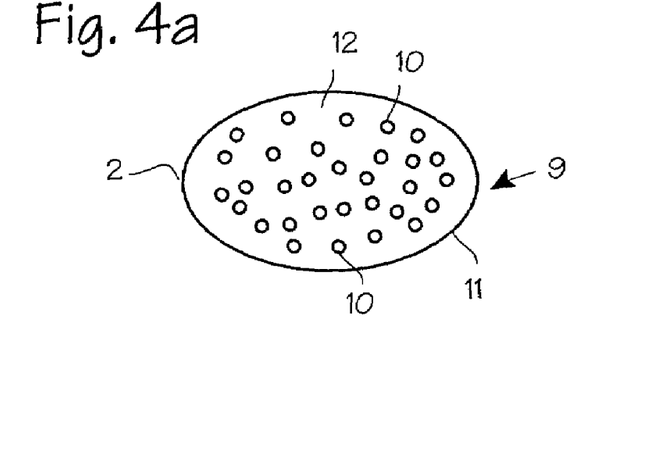
FIG. 4a is a top view of the hydrogel pad having a porous scrim and hydrogel dots.

FIG. 4a is a top view of a hydrogel patch 9 comprising of hydrogel dots or spheres 10 secured to a scrim 11. The scrim is made of a sufficiently porous material having a top surface 12 and a bottom surface 13. The scrim is a finely woven, nonconductive mesh of polyester, nylon, polyamide or similar materials. The mesh may have pore sizes in a large range. One suitable mesh is Saatifil PA 25/21, available from SaatiTech S.p.A of Italy. This mesh has a pore size of about 25 um and an open area of about 21%. The hydrogel pad is further comprised of hydrogel dots adhered to the top and bottom surfaces of the scrim. The porosity of the scrim permits the hydrogel dots to readily adhere to the scrim. The hydrogel dots are positioned on the surfaces of the scrim such that for each hydrogel dot on the top surface, there is a corresponding hydrogel dot positioned on the bottom surface and opposite to the hydrogel dot on the top surface. A suitable hydrogel is sold under the tradename Ludlow 62D, available from Ludlow Technical Products. This hydrogel is a moderately conductive hydrogel and has moderate adhesive qualities. The gel typically has an adhesive quality which makes easily releasable and applicable to the electrodes without need for tools. However, non-adhesive formulations of gel may be used if other means for releasable attachment are provided. Alternatively, conductive masses comprising masses of open cell foam or similar material may be loaded or saturated with conductivity gel or hydrogel, and used in place of the hydrogel dots 10 (this substitution may be made for all of the embodiments described below).

Figure 4B:
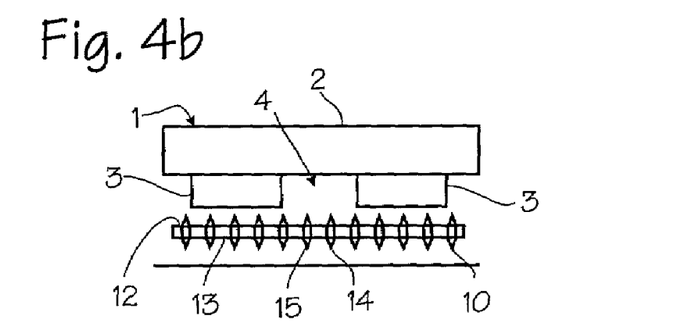
FIG. 4b is a cross-sectional side view of the hydrogel pad of FIG. 4a releasably applied to the electro-acupuncture device.

FIG. 4b is a cross sectional view of the hydrogel pad 9 of FIG. 4a capable of being releasably applied to the nerve-stimulation device 1. In cross section, the hydrogel dots on either side of the scrim form a mass of hydrogel which the scrim intersects, although the hydrogel is resident within the pores of the scrim to provide electrical conductivity through the scrim. The hydrogel permeates the pores, and, conversely, the scrim is disposed within the hydrogel. The hydrogel pad is applied to the device such that the hydrogel dots 10 on the top surface 12 of the scrim 11 contact the electrodes 3, and the hydrogel dots on the bottom surface 13 contact the skin when the device is secured to the wrist. As the hydrogel dots contact the electrodes and the skin, the hydrogel dots may deform (depending on composition). The positioning of the hydrogel dots on corresponding opposite surfaces of the scrim provide electrical conduction from the electrodes, through the hydrogel dots on the top surface of the scrim, through the hydrogel permeated through the pores of the scrim, through the hydrogel dots on the bottom surface of the scrim, and finally to the skin. The hydrogel dots are made in appropriate size and spaced sufficiently apart from each other on both surfaces so that if deformed under contact, the hydrogel dots 14 and 15 positioned between the electrodes, in the inter-electrode gap 4, do not contact each other to possibly bridge the electrodes. For a device designed for use on the wrist, the inter-electrode gap may range from about 0.1 to 0.5 inches (2–15 mm), so the width of the dots (relative to the plane established by the scrim and the electrodes) should be less than the chosen width of the inter-electrode gap. Preferably, the inter-electrode gap is about 0.18 inches (4–5 mm), and, accordingly, the width of the dots should be less than 0.18 inches. The active area of the patch, upon which the hydrogel dots are deposited, should be about the same, or slightly larger that the area of the electrodes, so the patch should be about 1 inch (2.5 cm) in diameter for use with the wrist-mounted electro-acupuncture device.

Figure 4C:
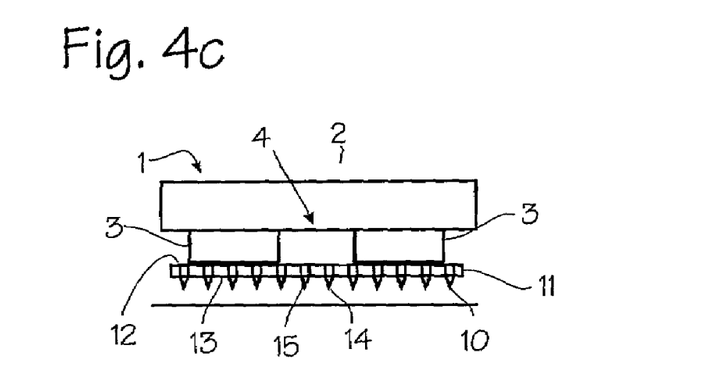
FIG. 4c is a side cross-sectional view of the hydrogel pad of FIG. 4a releasably applied to the electro-acupuncture device.

FIG. 4c is a cross sectional view of the hydrogel pad 9 of FIG. 4a with hydrogel dots secured to only the bottom surfaces of the scrim. The hydrogel pad is comprised of the sufficiently porous scrim 11 having the top surface 12 and the bottom surface 13. Hydrogel dots 10 are adhered to the bottom surface of scrim, with the hydrogel permeating into the pores of the scrim such that the hydrogel is present on both surfaces of the scrim. When the hydrogel pad is applied to the nerve-stimulation device 1, the hydrogel contacts the electrodes and there is electrical conduction from the electrodes, through the hydrogel permeated into the pores, through the hydrogel dots, and finally to the skin (when the device is secured to the wrist). Alternatively, the hydrogel dots could be adhered to the top surface of the scrim, with the hydrogel permeating into the pores of the scrim and present on both surfaces of the scrim.

Figure 5A:
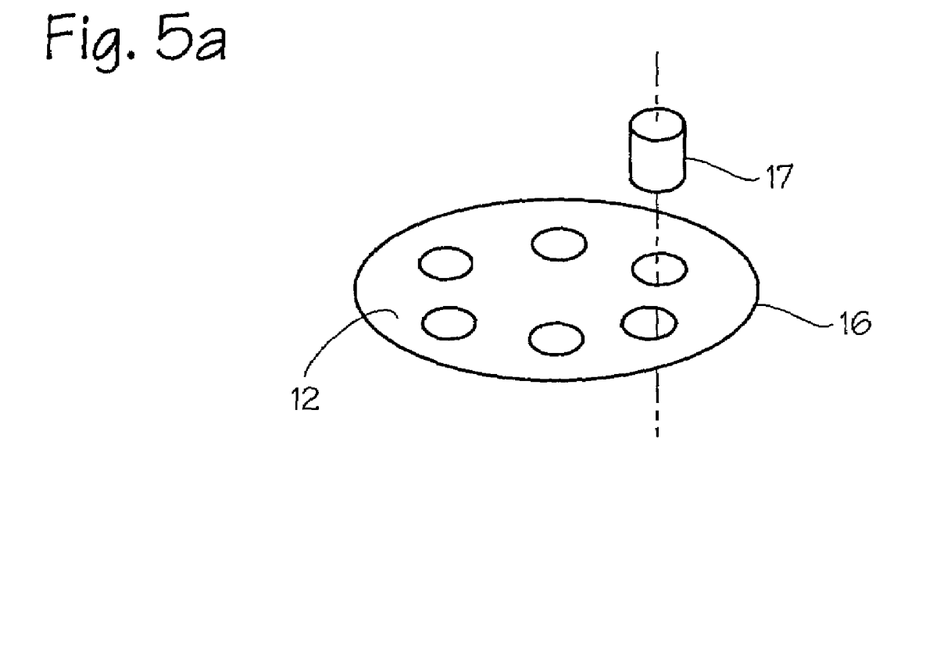

FIG. 5a is an exploded view of the hydrogel patch 9 having a hard carrier 16 and hydrogel plugs 17. The carrier has holes 18 punched through the carrier. The carrier need not be porous and may be made of a stiff plastic material, such as plastic that has been injection molded into a honeycomb matrix (see FIG. 10). The hydrogel plugs are sized to fit through the holes wherein the ends of the plugs are exposed through the top surface 12 and the bottom surface 13 of the carrier. The carrier in this embodiment may be made of a hard or nonporous plastic, such as PET or polyethylene.

Figure 5B:
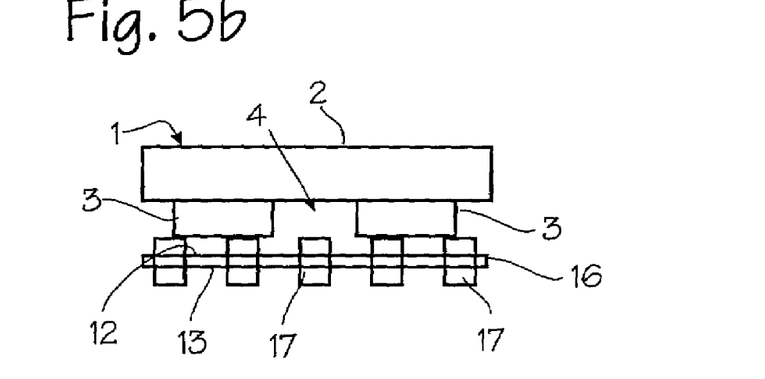
FIG. 5b a side cross-sectional view of the hydrogel pad of FIG. 5a releasably applied to the electro-acupuncture device.

FIG. 5b is a cross sectional view of the hydrogel pad 9 of FIG. 5a releasably applied to the nerve-stimulation device 1. The hydrogel pad is applied to the device 1 such that the ends of the hydrogel plugs 17 on the top surface 12 of the carrier 16 contact the electrodes 3, and the ends of the hydrogel plugs 17 on the bottom surface 13 may contact the skin when the device is applied to the body. When the hydrogel plugs 17 are placed between the electrodes and the skin, they establish an electrically conductive pathway from the electrodes, through the hydrogel plugs, and finally to the skin. The hydrogel plugs form a conductive layer between the electrodes and the skin. The hydrogel plugs may deform as they contact the electrodes and the skin. The holes of the carrier are spaced sufficiently apart so that if the hydrogel columns deform, the hydrogel columns resident in the inter-electrode gap 4 do not contact each other to possibly bridge the electrodes. Alternatively, the carrier can be sized and shaped (e.g. formed into the honey comb matrix) such that its thickness and the thickness of the hydrogel plugs are about the same. The similar thickness of the carrier and the plugs help prevent deformation of the plugs while still exposing sufficient hydrogel to achieve conductivity between the electrodes and the skin.

Figure 6A:
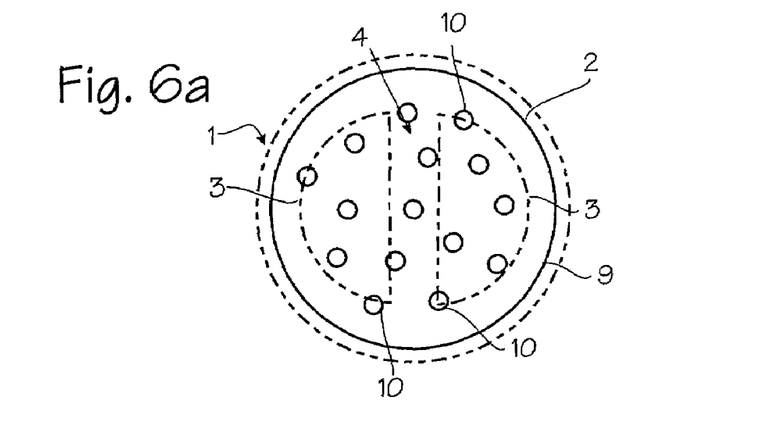
FIG. 6a is bottom view of the hydrogel pad with dots properly applied to the electro-acupuncture device.

FIG. 6a is a bottom view of hydrogel pad 9 of FIGS. 4a, 4c and 5a releasably applied to the nerve-stimulation device 1 (shown in phantom), wherein the pad is properly aligned with the device. The hydrogel dots 10 (or plugs 17) are sufficiently spaced apart so that if the hydrogel dots/plugs deform from contact with the electrodes 3 and skin, the hydrogel dots/plugs do not come into contact with each other, especially in the area between the electrodes, to possibly bridge the electrodes.

Figure 6B:
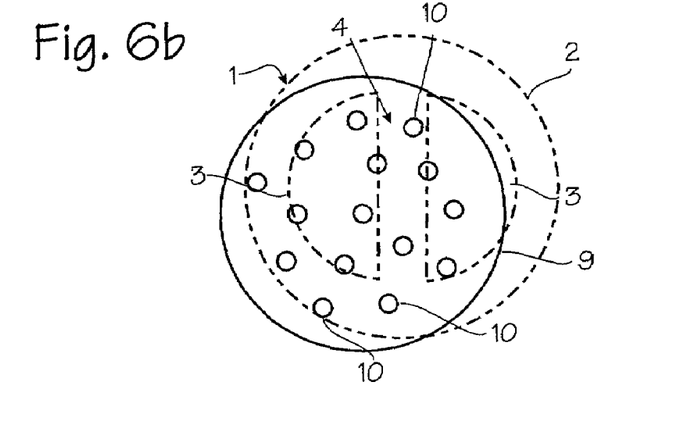
FIG. 6b is a bottom view of the hydrogel pad with dots applied off center to the electro-acupuncture device.

FIG. 6b is a bottom view of the hydrogel pad 9 of FIGS. 4a, 4c and 5a releasably applied to the nerve-stimulation device 1, wherein the pad is aligned off-center with the device. As seen in FIG. 6b, the spacing between the hydrogel dots/plugs prevents bridging between the electrodes even when the pad is aligned off-center to the device. Thus, even when grossly misaligned, the patch provides an adequate, non-shorting electrical pathway between the electrodes and the patient.

Figure 6C:
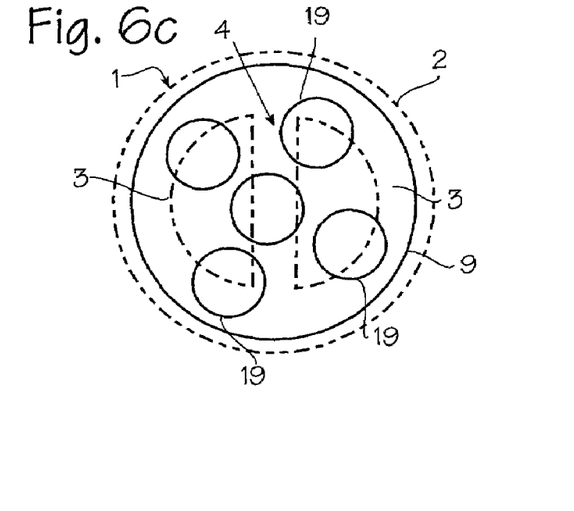
FIG. 6c is a bottom view of the hydrogel pad applied to the electro-acupuncture device.

FIG. 6c illustrates the limit of the size relationship between the hydrogel dots/plugs and the inter-electrode gap 4. In this example, the diameters of over-sized hydrogel dots/plugs 19 between the electrodes are larger than the inter-electrode gap. The hydrogel dots/plugs positioned in the inter-electrode gap bridge the electrodes to short the electrodes. To prevent bridging between the electrodes, the diameters of the hydrogel dots/plugs must be sufficiently smaller than the inter-electrode gap 4, even when the hydrogel dots/plugs are deformed under contact with the electrodes and skin.

Figure 7A:
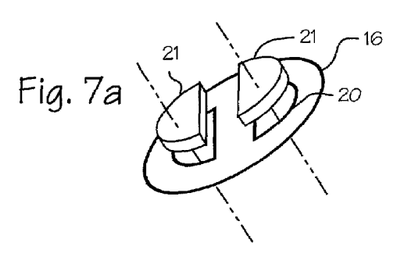
FIG. 7a is an exploded view of the hydrogel patch having D-shaped cutouts.
Figure 7B:
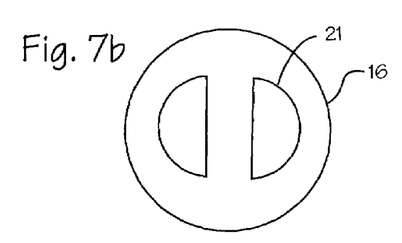
FIG. 7b is a top view of the hydrogel patch comprised of hydrogel pads sandwiched between two hard carriers.
Figure 7C:
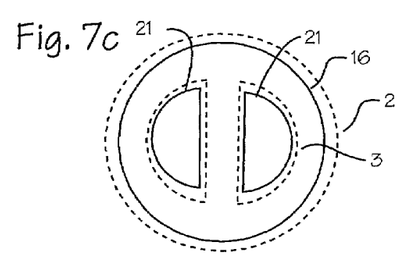
FIG. 7c is a bottom view of the hydrogel pad of FIG. 7a properly applied to the electro-acupuncture device.
Figure 7D:
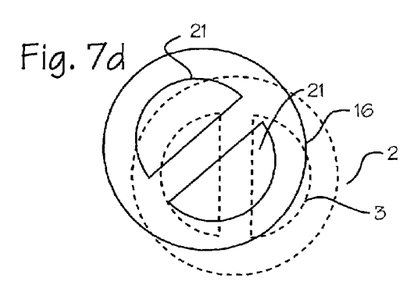
FIG. 7d is a bottom view of the hydrogel pad of FIG. 7a applied off center to the electro-acupuncture device.

FIGS. 7a, 7c and 7d illustrate the hydrogel patch 9 with electrode-shaped hydrogel pads. As shown in FIG. 7a, the hydrogel patch is comprised of the hard carrier 16 having cutouts 20 in the shape of the electrodes 3. In this example, the cutouts have a D-shape to match the shape of the electrodes. Also, the patch has a gap between the cutouts such that the separation between the cutouts is about the same as the separation between the electrodes (inter-electrode gap 4). Hydrogel pads 21 having shapes similar to the cutouts and the electrodes are secured to the carrier over the cutouts to cover the cutouts without contacting with each other. The hydrogel pads could either be secured to the top surface 12 of the carrier, the bottom surface 13 of the carrier, or alternatively to both surfaces. The hydrogel pads may be fixed over the cutouts by any suitable means. FIG. 7b shows the hydrogel patch of FIG. 7a as viewed from the top, with the gel pads 21 in place in the cut-outs of the carrier. Pads comprising open cell foam or similar material may be loaded or saturated with conductivity gel or hydrogel to form a conductive mass, and used in place of the D-shaped hydrogel pads.

FIG. 7c shows the hydrogel patch properly applied to the device. The separation or spacing between the electrode-shaped hydrogel pads prevents possible bridging of the electrodes by the hydrogel pads. There is electrical conduction from the electrodes, through the D-shaped hydrogel pads, and finally to the skin. The size of the gap between the hydrogel pads on the patch permits some misalignment, although gross alignment will result in the hydrogel pads bridging the electrodes. FIG. 7d illustrates the degree of misalignment necessary to bridge the inter-electrode gap with the hydrogel pads 21. The degree of misalignment may be significant without bridging the inter-electrode gap.

FIGS. 8a–8d illustrate the hydrogel pad 9 having the porous scrim and hydrogel strips. The hydrogel pad is comprised of the porous scrim (not shown) having a top surface (not shown) and a bottom surface (not shown). Hydrogel strips 22 are adhered to either the top or bottom surface of the scrim, with the hydrogel strips arranged parallel to each other. The strips are spaced apart such that the distance between the edges of any two strips is sufficient to ensure that the strips do not contact each other to short the electrodes. Also, the width of each strip is smaller than the inter-electrode gap. The hydrogel strips permeate into the pores of the scrim such that the hydrogel is present on both surfaces of the scrim.

Figure 8A:
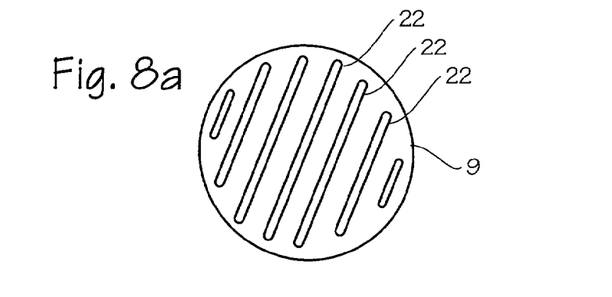
FIG. 8a is a top view of the hydrogel pad having the porous scrim and hydrogel strips.
Figure 8B:
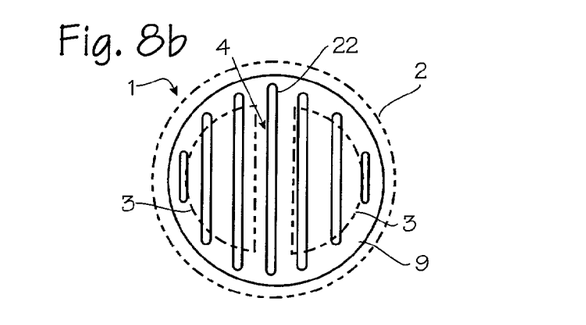
FIG. 8b is a bottom view of hydrogel pad of FIG. 8a properly applied to the electro-acupuncture device.
Figure 8C:
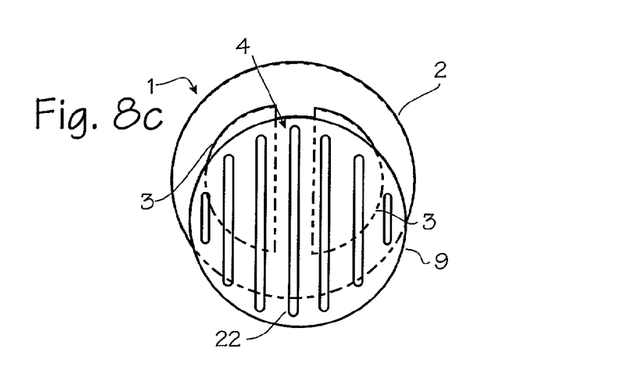
FIG. 8c is a bottom view of the hydrogel pad of FIG. 8a applied off center to the electro-acupuncture device.
Figure 8D:
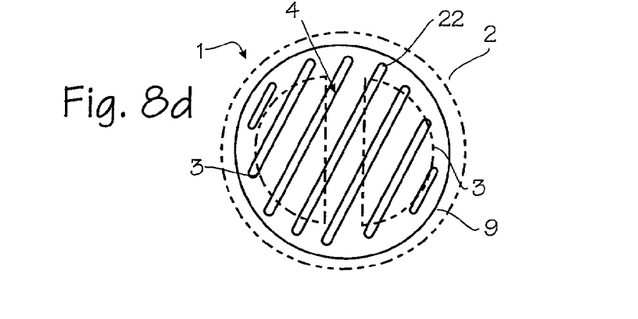
FIG. 8d is a bottom view of the hydrogel pad of FIG. 8a applied grossly off center to the electro-acupuncture device.

FIG. 8b shows the hydrogel pad of FIG. 8a properly applied to the device. The spacing between the hydrogel strips reduces or prevents the possibility of a short between the electrodes 3. Furthermore, because the width of each hydrogel strip is smaller than the inter-electrode gap, a hydrogel strip positioned between the electrodes will not bridge the electrodes to short the electrodes. There is electrical conduction from the electrodes, through the hydrogel strips, and finally to the skin. FIG. 8c shows the hydrogel pad applied off-center to the device. As seen, there is no bridging with this alignment. As long as the strips are aligned parallel to the long axis of the strips, the pad can be applied off-center yet maintain electrical conduction without bridging. The gaps between the hydrogel strips permit a large degree of misalignment and even gross misalignment of the pad across the electrodes without bridging of the electrodes. FIG. 8d shows that hydrogel pad applied off-center to the device. In this orientation, the hydrogel strips bridge the electrodes to short the electrodes.

Figure 9:
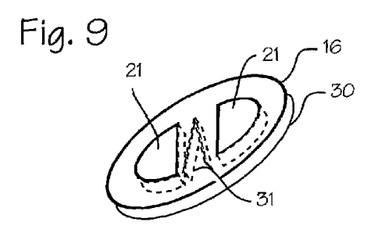
FIGS. 9 and 10 illustrates a hydrogel pad comprising a thick carrier.
Figure 10:
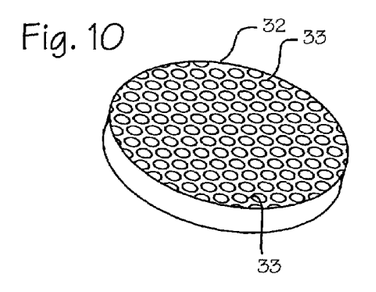

FIGS. 9 and 10 illustrate more structured embodiments of the hydrogel patch. The hydrogel patch of FIG. 9 is similar to the hydrogel patch of FIG. 7a, but includes a second carrier 30 with the D-shaped cut-outs positioned parallel to the first carrier 16, and connected to the first carrier with a brace or center stiffening member 31. The hydrogel pads 21 are sandwiched between the two carrier members such that surfaces of the hydrogel pads are exposed through the cutouts in each carrier. The stiffening member is sandwiched between the carriers and within the inter-electrode gap area, such that it is positioned between the hydrogel pads in the transverse direction. The stiffening member helps to prevent the hydrogel pads 21 from contacting each other and serves to stiffen the entire hydrogel patch. Also, when the stiffening member is aligned with the inter-electrode gap, the gel pads are sure to be properly placed over the electrodes. Indicia matching the brace may be placed on the housing, between the gaps, so that user may align the brace with the indicia, thereby ensuring proper alignment of the hydrogel pad.

FIG. 10 illustrates a carrier with a thickness matching the thickness of the gel spheres described in FIG. 4a or the plugs of FIG. 5a. The carrier 32 is thick as compared to the woven or plastic scrim of the prior embodiments, and may be extruded from a wide variety of plastics or gels or may be die-cut from suitable plastic, gel or foam material. Numerous passages, honeycombs, bores or the like (they may be any shape, though they are illustrated as circular holes) are provided in the carrier, and these passages are filled with the conductive masses of hydrogel 33. The passages may be filled with hydrogel in liquid form which is thereafter cured to form semi-solid plugs which fill the passages. The passages may also be filled with conductive masses comprising masses of open cell foam or similar material may be loaded or saturated with conductivity gel or hydrogel. The carrier and plugs may also be manufactured by co-extruding the hydrogel with a non-conductive carrier material, co-extruding normally non-conductive silicone as the carrier with a conductive silicone as the plugs, or with the same arrangement of polyurethane and conductive polyurethane or other non-conductive and conductive polymers and elastomers. The structure of the carrier prevents the numerous conductive masses from communicating with each other across the patch, while allowing conduction through the thickness of the patch. As with the previous embodiments, if the patch is designed for use on the wrist in conjunction with a wrist-mounted electro-acupuncture device with an inter-electrode gap in the range from 0.1 to 0.5 inches, the width of the conductive masses (relative to the plane established by the patch and the electrodes) should be less than the width of the inter-electrode gap. Preferably, the inter-electrode gap is about 0.18 inches, and, accordingly, the width of the conductive masses should be less than 0.18 inches.

While the preferred embodiments have been described in reference to the environment in which they were developed, they are merely illustrative of the principles of the inventions. Other embodiments and configurations may be devised without departing from the spirit of the inventions and the scope of the appended claims.

We claim:

1. An assembly for use with an electro-acupuncture device having at least two electrodes, said electrodes adapted to provide electrical stimulation to a user's skin when the device is secured to the skin, said electrodes defining an inter-electrode gap provided between the electrodes which separates the electrodes, said assembly comprising:

a scrim having a top surface and a bottom surface, said scrim provided with pores extending from the top surface to the bottom surface, wherein said top surface contacts the electrodes when the assembly is releasably applied to the electro-acupuncture device, and said bottom surface contacts the skin when the electro-acupuncture device is secured to the skin; and a plurality of masses of hydrogel disposed on the scrim and permeating into the pores of the scrim such that the masses of hydrogel are present on the top surface and the bottom surface of the scrim, wherein the masses of hydrogel are sized and positioned on the scrim such that, for at least one orientation of the scrim relative to the electrodes, any masses positioned within the inter-electrode gap when the assembly is releasably applied to the electro-acupuncture device do not bridge the electrodes, the masses of hydrogel are elongated strips having widths less than the inter-electrode gap even when deformed under contact with the electrodes and the skin.

2. The assembly of claim 1 wherein the masses of hydrogel are disposed on the top surface of the scrim, and said hydrogel permeates into the pores and being present at the bottom surface.

3. The assembly of claim 1 wherein the masses of hydrogel are disposed on the bottom surface of the scrim, said hydrogel permeating into the pores and being present at the top surface.

4. The assembly of claim 1 wherein the masses of hydrogel are disposed on the top surface and the bottom surface of the scrim, wherein for each mass of hydrogel disposed on the top surface there is a corresponding mass of hydrogel disposed on the opposite bottom surface.

5. The assembly of claim 1 wherein when the assembly is releasably applied to the device and the device is secured to the skin, the masses of hydrogel are capable of providing electrical conduction from the electrodes, through the masses of hydrogel, and to the skin.

6. The assembly of claim 1 wherein, when the assembly is releasably applied to the device and the device is secured to the skin, the masses of hydrogel are capable of providing an impedance matching layer between the electrodes and the skin.

7. An assembly for use with an electro-acupuncture device having at least two electrodes, said electrodes adapted to provide electrical stimulation to a user's skin when the device is secured to the skin, said electrodes defining an inter-electrode gap provided between the electrodes which separates the electrodes, said assembly comprising:

a scrim having a top surface and a bottom surface, said scrim provided with pores extending from the top surface to the bottom surface, wherein said top surface contacts the electrodes when the assembly is releasably applied to the electro-acupuncture device, and said bottom surface contacts the skin when the electro-acupuncture device is secured to the skin; and a plurality of masses of hydrogel disposed on the scrim and permeating into the pores of the scrim such that the masses of hydrogel are present on the top surface and the bottom surface of the scrim wherein the masses of hydrogel are sized and dimensioned as dots having diameters less than the inter-electrode gap on the scrim such that, for at least one orientation of the scrim relative to the electrodes, any masses positioned within the inter-electrode gap when the assembly is releasably applied to the electro-acupuncture device do not bridge the electrodes.

* * * * *